Figure 1:
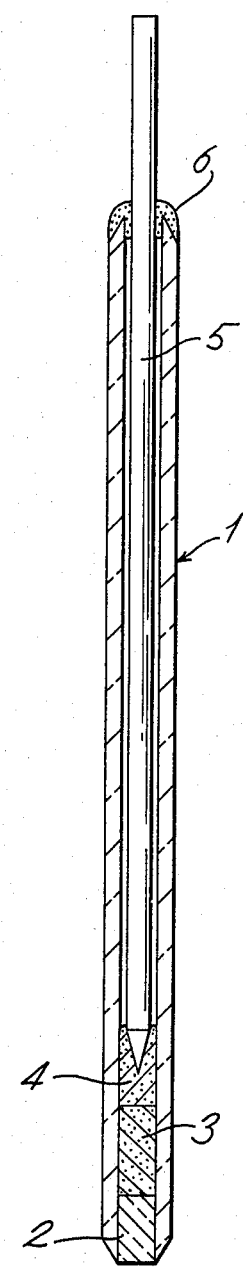

United States Patent [19]

Fray

[11] 4,217,179
[45] Aug. 12, 1980

[54] DETERMINATION OF LITHIUM, SENSOR THEREFOR AND METHOD OF MAKING SAID SENSOR

[75] Inventor: Derek J. Fray, Cambridge, England

[73] Assignee: National Research Development Corporation, London, England

[21] Appl. No.: 54,579

[22] Filed: Jul. 3, 1979

[30] Foreign Application Priority Data

Jul. 17, 1978 [GB] United Kingdom ............... 30028/78

[51] Int. Cl.² .......................................... G01N 27/58
[52] U.S. Cl. .................................. 204/1 T; 106/39.7; 204/195 G; 204/195 S
[58] Field of Search ............... 204/1 A, 195 S, 195 G; 106/39.7

[56] References Cited

U.S. PATENT DOCUMENTS 3,143,488  8/1964  Arthur et al. ........................ 204/1 A
3,862,016  1/1975  Arthur et al. ........................ 204/1 A Primary Examiner—G. L. Kaplan
Attorney, Agent, or Firm—Oblon, Fisher, Spivak, McClelland & Maier

[57] ABSTRACT

Apparatus for determining the lithium content of a substance by monitoring the e.m.f. generated between the substance and a reference material containing lithium, the substance and reference being separated from one another by a solid electrolyte which is electrically conductive to lithium ions, comprises a probe adapted to contain the reference material and to separate the reference material from the substance when the probe is introduced thereto, and in which the solid electrolyte of the probe comprises $\beta$-spodumene; a preferred tubular probe form of said apparatus being produced by a process in which a pellet of $\beta$-spodumene is fabricated in situ in the end of a tube of refractory material. In addition, a process for the determination of lithium present in a substance comprises determining the e.m.f. generated between the substance and a reference material containing lithium, in which the reference material and substance are separated by a solid electrolyte comprising $\beta$-spodumene.

13 Claims, 2 Drawing Figures

DETERMINATION OF LITHIUM, SENSOR THEREFOR AND METHOD OF MAKING SAID SENSOR

This invention relates to the determination of lithium, normally in the presence of other materials, and in particular to the determination of the lithium content of molten metals and alloys e.g. molten aluminium.

During the commercial smelting of aluminium in Hall cells lithium salts are added to the cells to raise the conductivity of the electrolyte and thereby reduce power consumption. Lithium, even in low quantities, however, drastically alters the casting properties of molten aluminium and the surface finish of some alloys. It is thus highly desirable to be able to quickly and simply measure and therefore control the lithium content of molten metals such as aluminium.

The specification of our U.K. Pat. No. 1,470,558 describes a method and apparatus for detecting and determining elements in the presence of other materials based on a galvanic method using $\beta$-alumina solid electrolyte probes. In this prior specification, it is proposed that a lithium $\beta$-alumina probe may be used for the determination and detection of lithium. Lithium $\beta$-alumina, however, is not wholly suitable for use in the construction of such a probe due to its brittle nature. In addition, at the elevated temperatures of molten metals, lithium $\beta$-alumina is liable to revert to sodium beta-alumina in the presence of the sodium which always occurs in molten aluminium from aluminium smelting sources.

A solid electrolyte probe has now been developed which is particularly suitable for use for the determination of lithium in the presense of molten metals or alloys, and which does not suffer from the deficiencies of the lithium $\beta$-alumina solid electrolyte material.

Accordingly the present invention comprises apparatus in the form of a probe for determining the lithium content of a substance by monitoring the e.m.f. generated between the substance and a reference material containing lithium, the substance and reference being separated from one another by a solid electrolyte which is electrically conductive to lithium ions, in which the probe is adapted to contain the reference material and to separate the reference material from the substance when the probe is introduced thereto, and in which the solid electrolyte comprises $\beta$-spodumene.

The invention also includes a process for the determination of lithium present in a substance comprising determining the e.m.f. generated between the substance and a reference material containing lithium, in which the reference material and substance are separated by a solid electrolyte comprising $\beta$-spodumene.

$\beta$-spodumene is a compound comprising a $Li_2O/Al_2O_3/SiO_2$ mixture and having the approximate composition $Li_2O \cdot Al_2O_3 \cdot 4SiO_2$ which may, however, vary widely. For example, characteristic $\beta$-spodumene compositions are described in the paper by Roy and Osborn (Rustum Roy and E. F. Osborn, J. Am. Chem Soc. 71 (6) 2086 to 2095 (1949) especially in the tertiary phase diagram at page 2092 thereof. $\beta$-spodumene compositions in general, such as those falling within the $\beta$-spodumene area of the above tertiary phase diagram, are suitable for use as the solid electrolyte of the present invention.

The probe of the invention may take any suitable form for containing the reference material and separating the reference material from the substance when the probe is introduced thereto. It will be appreciated, however, that the probe of the invention is preferably intended for use in high temperature environments, in particular for use in determining lithium in molten metals such as molten aluminium e.g. at temperatures of about 700° C., usually at least 600° C. and often 750°–800° C. or higher. Thus the probe usually comprises a housing which is stable at such elevated temperatures, e.g. a housing constructed from a refractory material.

In a preferred embodiment the probe takes the form of a tube closed at one end, preferably a tube of refractory material e.g. silica or $\alpha$-alumina, closed at one end with a pellet of $\beta$-spodumene, and in this preferred construction, the pellet of $\beta$-spodumene may be fabricated in situ in the end of the tubular probe. For instance, hot pressing of $\beta$-spodumene powder may be employed, though in a particularly preferred embodiment $\beta$-spodumene powder is fused into the end of the tube to form the pellet. For example, $\beta$-spodumene powder is lightly packed into the end of the tube which is then heated to fuse the powder into the form of a pellet. Usually, the powder is heated to white heat in a gas flame, and it has been found to be particularly advantageous to quench the pellet from red heat immediately following fusion. In addition to providing a good seal between pellet and tube such fusion treatment and quenching advantageously provides an electrolyte pellet in which the $\beta$-spodumene is in the form of a glass having desirable conductivity properties.

Any suitable reference material comprising lithium may be used, though usually the reference material is a solid. Characteristically the reference material is a three-phase material to satisfy equilibrium requirements. Preferably a three-phase solid reference material is used comprising $\beta$-spodumene, and for example, a mixture of $\beta$-spodumene/$Li_2O \cdot SiO_2$/$Li_2O \cdot 2SiO_2$ has been found to be particularly suitable. It will be appreciated, however, that in order for the reference material to provide a stable response it is necessary to maintain a constant oxygen potential i.e. partial pressure over the reference material. The constant oxygen partial pressure may be supplied by the ambient atmosphere, though preferably, especially when the reference material is sealed within the probe, the probe contains, in addition to the reference material, a second solid material which provides a fixed oxygen potential within the probe i.e. oxygen partial pressure at a given temperature. In a preferred embodiment this second solid material comprises a metal/metal oxide mixture, such as a $Cu/Cu_2O$, $Cr/Cr_2O_3$ or especially a Ni/NiO mixture.

The probe of the invention is usually provided with an internal electrode, such as a stainless steel rod which is inserted into the probe to make electrical contact with the internal surface of the $\beta$-spodumene electrolyte. Such an internal electrode may be sealed into the probe e.g. preferred tubular probe, for instance by means of a suitable cement, such as a heat resistant cement. In use, an external electrode e.g. a stainless steel rod, is also provided and the e.m.f. generated between the internal and external electrodes is monitored, preferably using a high impedance voltmeter.

Figure 2:
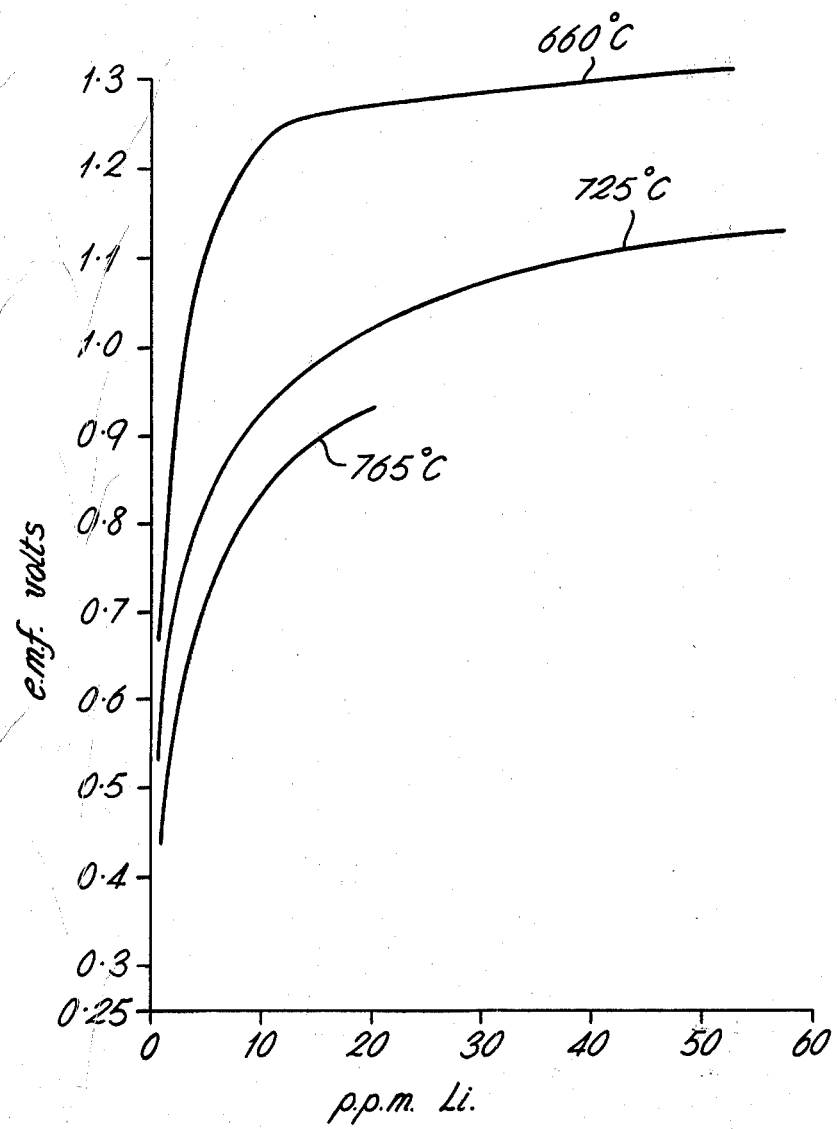

The invention is further described by way of illustration only in the following example, with reference to the accompanying diagrams, in which FIG. 1 represents a vertical section through a sealed tubular probe according to the invention; and FIG. 2 is a graph of the e.m.f. obtained when using the probe of FIG. 1 to measure the lithium content of a molten aluminium bath at various temperatures and using a Ni/NiO mixture to control the oxygen pressure over the reference material.

EXAMPLE

With reference to FIG. 1 a preferred form of tubular probe according to the invention is constructed as follows. β-spodumene powder of approximate composition $Li_2O.Al_2O_3.4SiO_2$ is lightly compacted by hand into one end of a silica tube 1 (length 8 cm, external diameter 4 mm, internal diameter 2 mm) to a depth of about 2–3 mm. This end of the silica tube 1 is then held in a natural gas-oxygen flame and the β-spodumene electrolyte powder fused to give a β-spodumene pellet 2 sealing one end of the tube 1. The correct period for the fusion treatment is judged by careful visual observation, through dark glasses, of the heated end of the silica tube 1 the treatment being continued until a brightly luminous continous band of fused material is seen to encircle the β-spodumene pellet 2. During the fusion treatment the β-spodumene powder fuses and reacts with the silica of the tube 1 such that the composition of the β-spodumene in the pellet 2 is slightly altered with respect to the powder starting material. After removal from the flame the end of the tube 1 is allowed to cool to a dull red heat and is then rapidly quenched by plunging into cold water. The external fused surface coating of the β-spodumene pellet 2 is then removed by grinding against emery paper, the end of the tube 1 being slightly bevelled around its edge. After quenching, the β-spodumene of pellet 2 is found to be a glass having advantageous conductivity properties for lithium ions as compared with crystalline β-spodumene.

A 1:1:1 mixture of powdered β-spodumene/$Li_2O.SiO_2$/$Li_2O.2SiO_2$ three phase reference material is then introduced into the tube 1 via its open end and packed down to give a layer 3 of depth about 10 mm. A similar amount of powdered 1:1 nickel/nickel oxide mixture is packed on top of the layer of reference material 3 to provide a layer of material 4 which stabilises the oxygen potential within the probe during use. It will be appreciated, however, that the relative proportions of metal and metal oxide in the oxygen potential stabiliser 4 are not critical and may be varied widely. The layers of reference material 3 and oxygen potential stabiliser 4 are finally rammed home with a silver steel rod 5 (length 8 mm, diameter 2 mm) which has been ground to a point at its end. The rod 5 which provides the internal electrode of the probe is cemented into the open end of the tube 1 with "Autostic" heat-resistant cement 6 thus making the probe airtight.

A probe as described above is connected across a high impedance voltmeter with a steel rod external electrode (not shown). The probe and external electrode are dipped into molten aluminium baths maintained at three different temperatures, 765° C., 725° C. and 660° C., and the e.m.f. readings taken. The lithium contents of the molten aluminium baths are varied by adding lithium metal. Bath samples are withdrawn corresponding to each e.m.f. reading and the lithium contents of the baths determined by conventional chemical analysis techniques. The results obtained are given in FIG. 2 which shows curves of the e.m.f. readings (volts) obtained against the lithium content (ppm) of the molten aluminium baths at the three chosen temperatures.

I claim:

1. Apparatus in the form of a probe for determining the lithium content of a substance by monitoring the e.m.f. generated between the substance and a reference material containing lithium, the substance and reference being separated from one another by a solid electrolyte which is electrically conductive to lithium ions, in which the probe contains the reference material and separates the reference material from the substance with said solid electrolyte when the probe is introduced thereto, and in which the solid electrolyte of the probe comprises β-spodumene.

2. Apparatus according to claim 1, in which the probe comprises a temperature stable housing in the form of a tube of refractory material closed at one end with a pellet of beta-spodumene.

3. Apparatus according to claim 2, in which the beta-spodumene pellet is fused into the end of the refractory tube.

4. Apparatus according to claim 1, in which the probe contains a three-phase reference material comprising lithium.

5. Apparatus according to claim 4, in which the reference material comprises a mixture of β-spodumene/$Li_2O.SiO_2$/$Li_2O.2SiO_2$.

6. Apparatus according to claim 1, in which the probe contains, in addition to the reference material, a second solid material which provides a fixed oxygen potential within the probe.

7. Apparatus according to claim 6, in which the second solid material comprises a $Cu/Cu_2O$, $Cr/Cr_2O_3$ or a Ni/NiO mixture.

8. A process for the production of apparatus according to claim 1, in which a pellet of β-spodumene is fabricated in situ in the end of a tube of refractory material to provide a tubular probe.

9. A process according to claim 8, in which the pellet of β-spodumene is fabricated by hot pressing of β-spodumene powder.

10. A process according to claim 8, in which the pellet of β-spodumene is fabricated by fusing β-spodumene powder into the end of the tube of refractory material to form a pellet.

11. A process according to claim 10, in which the pellet is quenched from red heat immediately following fusion.

12. A process for the determination of lithium present in a substance, which comprises determining the e.m.f. generated between the substance and a reference material containing lithium, in which the reference material and substance are separated by a solid electrolyte comprising β-spodumene.

13. A process according to claim 12, in which the substance comprises a molten metal.

* * * * *